(12) United States Patent
Dal Lago et al.

(10) Patent No.: US 10,271,589 B2
(45) Date of Patent: Apr. 30, 2019

(54) SMART SAFETY GARMENT WITH SIGNAL LIGHTS

(71) Applicant: CLARA SWISS TECH SAGL, Lugano (IT)

(72) Inventors: Marco Dal Lago, Maccagno (IT); Paolo Cunzolo, Varese (IT); Gianluca Costante, Tenero (CH); Gian Mattia Pettinato, Luino (IT)

(73) Assignee: CLARA SWISS TECH SAGL, Lugano (CH)

(*) Notice: Subject to any disclaimer, the term of this patent is extended or adjusted under 35 U.S.C. 154(b) by 0 days.

(21) Appl. No.: 15/756,238

(22) PCT Filed: Aug. 31, 2015

(86) PCT No.: PCT/EP2015/069830
§ 371 (c)(1),
(2) Date: Feb. 28, 2018

(87) PCT Pub. No.: WO2017/036507
PCT Pub. Date: Mar. 9, 2017

(65) Prior Publication Data
US 2018/0242658 A1  Aug. 30, 2018

(51) Int. Cl.
*A41D 13/01* (2006.01)
*A41D 1/00* (2018.01)
(Continued)

(52) U.S. Cl.
CPC ............. *A41D 13/01* (2013.01); *A41D 1/002* (2013.01); *A41D 1/04* (2013.01); *B60Q 1/2673* (2013.01);
(Continued)

(58) Field of Classification Search
CPC combination set(s) only.
See application file for complete search history.

(56) References Cited

U.S. PATENT DOCUMENTS

| 2002/0044052 A1* | 4/2002 | Stewart | A41D 13/01 340/475 |
| 2004/0156215 A1* | 8/2004 | Wooldridge | A41D 13/01 362/570 |

(Continued)

FOREIGN PATENT DOCUMENTS

| EP | 2862748 A1 | 4/2015 |
| GB | 2494917 A | 3/2013 |

OTHER PUBLICATIONS

International Search Report dated May 10, 2016 re: Application No. PCT/EP2015/069830; pp. 1-4; citing: US 2010/309009 A1, US 2010/251453 A1, GB 2 494 917 A and EP 2 862 748 A1.
(Continued)

*Primary Examiner* — Travis R Hunnings
(74) *Attorney, Agent, or Firm* — Cantor Colburn LLP (57) ABSTRACT

A smart safety garment with signal lights includes a basic garment, at least a pair of turn signal lights embedded on the external surface of the basic garment, and an electronic assembly for the control. The management and monitoring of the smart safety garment includes a control unit, the at least a pair of turn signal lights being connected or connectable to the control unit. The electronic assembly further includes a braking sensor connected or connectable to the control unit and adapted to perceive a deceleration and to generate a corresponding braking signal intended to the control unit. The control unit is configured to power up at least a pair of turn signal lights according to the braking signal.

15 Claims, 4 Drawing Sheets

(51) Int. Cl.

| | | |
|---|---|---|
| *B60Q 1/26* | (2006.01) | |
| *B62J 6/00* | (2006.01) | |
| *G08B 5/00* | (2006.01) | |
| *B62J 99/00* | (2009.01) | |
| *G09F 9/305* | (2006.01) | |
| *G09F 13/22* | (2006.01) | |
| *G09F 21/02* | (2006.01) | |
| *A41D 1/04* | (2006.01) | |
| *B62J 6/16* | (2006.01) | |
| *A61B 5/024* | (2006.01) | |
| *G06F 1/16* | (2006.01) | |

(52) U.S. Cl.
CPC ............... *B62J 6/005* (2013.01); *B62J 6/16* (2013.01); *B62J 99/00* (2013.01); *G08B 5/004* (2013.01); *G09F 9/305* (2013.01); *G09F 13/22* (2013.01); *G09F 21/02* (2013.01); *A41D 2600/104* (2013.01); *A61B 5/02438* (2013.01); *B60Q 2900/30* (2013.01); *B62J 2006/006* (2013.01); *B62J 2006/008* (2013.01); *B62J 2099/002* (2013.01); *B62J 2099/008* (2013.01); *G06F 1/163* (2013.01); *G09F 2009/3055* (2013.01); *G09F 2013/222* (2013.01); *G09F 2021/023* (2013.01)

(56) References Cited

U.S. PATENT DOCUMENTS

| | | | | |
|---|---|---|---|---|
| 2007/0063831 A1* | 3/2007 | Perkins | ............... | B60Q 1/2673 340/479 |
| 2008/0089056 A1* | 4/2008 | Grosjean | ............. | B60Q 1/2673 362/103 |
| 2010/0251453 A1* | 10/2010 | Chen | ................ | B60Q 1/2673 2/69 |
| 2010/0253501 A1* | 10/2010 | Gibson | ............... | A41D 13/01 340/475 |
| 2010/0309009 A1* | 12/2010 | Lee | ................. | B60Q 1/2673 340/665 |
| 2014/0254143 A1* | 9/2014 | Wansor | ............. | F21V 33/0008 362/103 |
| 2015/0016095 A1* | 1/2015 | Kretzu | ................. | A41D 1/002 362/108 |
| 2015/0250043 A1* | 9/2015 | Timmerberg | ........... | B62J 6/005 315/153 |
| 2015/0276202 A1* | 10/2015 | Haslem, Sr. | ......... | F21V 33/0008 362/108 |
| 2016/0068214 A1* | 3/2016 | Tang | ....................... | B62J 6/00 362/108 |
| 2016/0144775 A1* | 5/2016 | Ejiawoko | .......... | A41D 13/01 340/465 |

OTHER PUBLICATIONS

Written Opinion dated May 10, 2016 re: Application No. PCT/EP2015/069830; pp. 1-5; citing: US 2010/309009 A1, US 2010/251453 A1 and GB 2 494 917 A.

\* cited by examiner

SMART SAFETY GARMENT WITH SIGNAL LIGHTS

TECHNICAL FIELD

The present disclosure generally relates to a smart safety garment with signal lights, and particularly, but not exclusively, to a smart safety garment with signal lights for cyclists.

BACKGROUND

Nowadays, population growth and urbanisation are two of the most important reason that are promoting walking and the use of the bicycle as easy and low-cost choices for the transportation in the cities. For example, in 2010 the bicycle was the primary means of transport for more than 35 million Europeans or 7.4% of the total European population.

While cycling and walking have beneficial effects both on the health of the people and on the preservation of the environment, the on-going increment of city traffic poses a major threat to the safety of urban cyclists and pedestrians. For example, in 2010 thousands of cyclists and pedestrians died in road accidents in Europe, in particular 1.994 cyclists and 6.004 pedestrians.

Researches show that one of the major causes of collision of cyclists and pedestrians with cars is due to poor light conditions along the streets, in particular during night time. In fact, although only 10% of the overall bicycle rides take place during night-time, around 30% of car-on-bike road accidents occur during night time. And around 50% of car-on-pedestrian road accidents occur during night time.

Despite these alarming numbers, up to 40% of cyclists ride in the dark without lights or with partially defective lights. Moreover, a large number of recent studies show that these road accidents occur more frequently in urban areas and close to intersections.

In the state of the art, devices and systems are known for the light signaling of the presence of a cyclist or a pedestrian along the street. Devices and systems are also known for the light indication of the direction that the cyclist or the pedestrian intends to follow.

However, these known devices and systems present some disadvantages. In fact, they offer to urban cyclists and pedestrians a low visibility along streets with poor light conditions, in particular from long distances. Such a disadvantage is due to the fact that the known devices and systems for the light signaling of a cyclist or a pedestrian are equipped with inadequate brightness lights.

Moreover, these known devices and systems are controlled manually, without any kind of smart or automatic activation, and their signal lights work only as a result of a command by the cyclist or the pedestrian, which often has to perform complex movements in order to control them, even releasing the handlebars of the bicycle or looking away from the street.

SUMMARY

The aim of the present disclosure is to provide a smart safety garment with signal lights that is capable of improving the background art in one or more of the aspects indicated above.

Within the scope of this aim, the disclosure provides a smart safety garment with signal lights that allows to improve the safety of urban cyclists and pedestrians, such as runners and joggers, enhancing their visibility along streets with poor light conditions, also from long distances.

In particular, the disclosure provides a smart safety garment with signal lights that permits a cyclist or a pedestrian to not worry about the control of the signal lights, automating and simplifying their operation.

Moreover, the present disclosure provides a smart safety garment with signal lights that allows a cyclist to not move his/her hands from the handlebars of the bicycle, if he/she needs to directly control the signal lights.

The present disclosure also provides a smart safety garment with signal lights that shields cyclists and pedestrians from adverse weather conditions and atmospheric agents such as rain, wind, snow, and so on.

The present disclosure further provides a smart safety garment with signal lights that is highly reliable, relatively easy to manufacture and at competitive costs.

This aim, as well as these and other advantages that will become better apparent hereinafter, are achieved by providing a smart safety garment with signal lights, comprising a basic garment, at least a pair of turn signal lights embedded on the external surface of said basic garment, and an electronic assembly for the control, the management and the monitoring of said smart safety garment comprising a control unit, said at least a pair of turn signal lights being connected or connectable to said control unit, characterized in that said electronic assembly further comprises a braking sensor, connected or connectable to said control unit, adapted to perceive a deceleration and to generate a corresponding braking signal intended to said control unit, said control unit being configured to power up said at least a pair of turn signal lights according to said braking signal.

BRIEF DESCRIPTION OF THE DRAWINGS

The foregoing, as well as further characteristics and advantages of the present disclosure, will become better apparent to those skilled in the art from the following description of a preferred, but not exclusive, embodiment of the smart safety garment with signal lights according to the disclosure, illustrated by way of nonlimiting example in the accompanying drawings, wherein.

DETAILED DESCRIPTION OF THE DRAWINGS

The following detailed description and appended figures describe and illustrate an exemplary embodiment of the disclosure. The description and figures serve to enable one skilled in the art to make and use the disclosure, and are not intended to limit the present disclosure, and its applications or uses. It should also be understood that throughout the figures, corresponding reference numerals indicate like or corresponding parts and features.

With reference to FIGS. 1-4, a smart safety garment with signal lights according to the disclosure, generally designated by the reference numeral 10, comprises substantially a basic garment 12, such as a jacket, a first pair of turn signal lights 14, a second pair of turn signal lights 16, both the first 14 and the second 16 pairs being embedded on the external surface of the basic garment 12, an electronic assembly 60 for the control, the management and the monitoring of the smart safety garment 10 itself, and control means operable by a user, such as a cyclist 50 or a pedestrian 56, wearing the smart safety garment 10 with signal lights according to the disclosure.

In a preferred embodiment, the basic garment 12 may be constituted by a weatherproof jacket, completely waterproof and windproof. In this case, thanks to the smart safety garment 10, the user 50, 56 doesn't have to care about adverse weather conditions when he/she is along the streets, and the electronic assembly 60 is carefully protected by atmospheric agents, hidden and covered within the weatherproof jacket.

In an alternative embodiment of the smart safety garment 10 according to the disclosure, the basic garment 12 may be constituted by a backpack cover. In this case the backpack cover, which has a smaller size than a jacket, can be folded and stowed in the backpack itself after its use.

In another alternative embodiment of the disclosure, the basic garment 12 may be constituted by a belt. In this case, it is preferable to include only one pair of turn signal lights in the smart safety garment 10, because of the limited belt surface.

The first pair of turn signal lights 14 is placed and embedded on the back of the basic garment 12. In an embodiment, the signal lights 14 are in the form of arrowheads, the one 14a oriented towards the right and the other 14b oriented towards the left.

The second pair of turn signal lights 16 is placed and embedded on the sleeves of the basic garment 12. In an embodiment, the turn signal lights 16 surround the upper arm such that the one 16a is oriented towards the right and the other 16b is oriented towards the left. In particular, this second pair of turn signal lights 16 placed on the sleeves of the basic garment 12 is useful when the user 50, 56 wears a backpack, which covers the first pair of turn signal lights 14, thus improving the overall visibility of the user 50, 56.

Both the first 14 and the second 16 pairs of turn signal lights are connected or are connectable to the electronic assembly 60 for the control, the management and the monitoring of the smart safety garment 10.

In a preferred embodiment of the smart safety garment 10 according to the disclosure, all or some of the turn signal lights 14 and 16 may include multi-color (RGB) light emitting diodes (LEDs). The use of LEDs for the light emission advantageously provides for a high brightness level with a low energy consumption.

In a more preferred embodiment of the disclosure, the light emitted by the above LEDs may be diffused into an optical flat light guide, for example a guide for each turn signal light 14a, 14b, 16a, or 16b, resulting in a flexible jacket.

The optical flat light guide comprises a light-conducting flexible fiber. This fiber, when fed by a light source, like the above LEDs, at one of its ends, produces 360-degree diffused light.

More generally, the turn signal lights 14 and 16 embedded on the external surface of the basic garment 12, enable the user 50, 56 to be seen from a long distances by drivers thereby preventing road accidents and consequent physical and material damages.

In a preferred embodiment of the smart safety garment 10 according to the disclosure, the control means for the control of the turn signal lights 14, 16 may comprise a remote control 20 operable by the cyclist 50 and placed or placeable on the handlebars 54 of the bicycle 52.

When the cyclist 50 wants to change direction, turning right or left, he/she can simply power up the turn signal lights 14 and 16 corresponding to the desired direction (right: 14a and 16a; left: 14b and 16b) by acting on the remote control 20 placed or placeable on the handlebars 54 of the bicycle 52.

The remote control 20 is wireless. The remote control 20 is easily removable from the handlebars 54 of the bicycle 52, thanks to its shape and its design.

The remote control 20 comprises a battery, for example a button cell battery, ensuring a long activity period. The remote control 20 preferably has low-power consumption.

In order to perform the wireless transmission of the command signals, such as RF signals, that are generated by the remote control 20 operated by the cyclist 50 and that carry the commands for the control of the turn signal lights 14 and 16, the remote control 20 further comprises, or is connected to, an antenna for transmitting the RF command signals to the electronic assembly 60.

In summary, these commands are sent from the remote control 20 to the electronic assembly 60 of the smart safety garment 10 by means of the respective antennas, for example RF antennas.

The remote control 20 enables the cyclist 50 to interacting with the smart safety garment 10 with signal lights without having to move his/her hands from the handlebars 54 of the bicycle 52.

In a more preferred embodiment, the remote control may comprise a lever 22. In this case, if the cyclist 50 moves the lever 22 to the right, he/she commands to power up the turn signal lights 14a and 16a on the right side of the basic garment 12; while, if the cyclist 50 moves the lever 22 to the left, he/she commands to power up the turn signal lights 14b and 16b on the left side of the basic garment 12.

In another preferred embodiment of the disclosure, the control means of the smart safety garment 10 with signal lights may comprise a switch or button, connected or connectable to the control unit 62, operable by the cyclist 50 or by the pedestrian 56, and placed directly on the basic garment 12. This switch or button is adapted to generate a command signal intended to the control unit 62, in order to power up the turn signal lights 14 and 16 according to this command signal, without using the remote control 20.

The above switch or button may allow the user 50, to power up the turn signal lights 14 and 16 according to several activation modes, for example either in solid mode or in strobe mode (see below).

The above feature makes the smart safety garment 10 a useful asset also for urban pedestrians, such as runners and joggers, who recognize the importance of a good visibility along streets with poor light conditions.

As mentioned, the electronic assembly 60 for the control, the management and the monitoring of the smart safety garment 10 is preferably hidden and covered within the basic garment 12, for example being enclosed in a protection case embedded on the internal surface of the basic garment 12.

Figure 1:
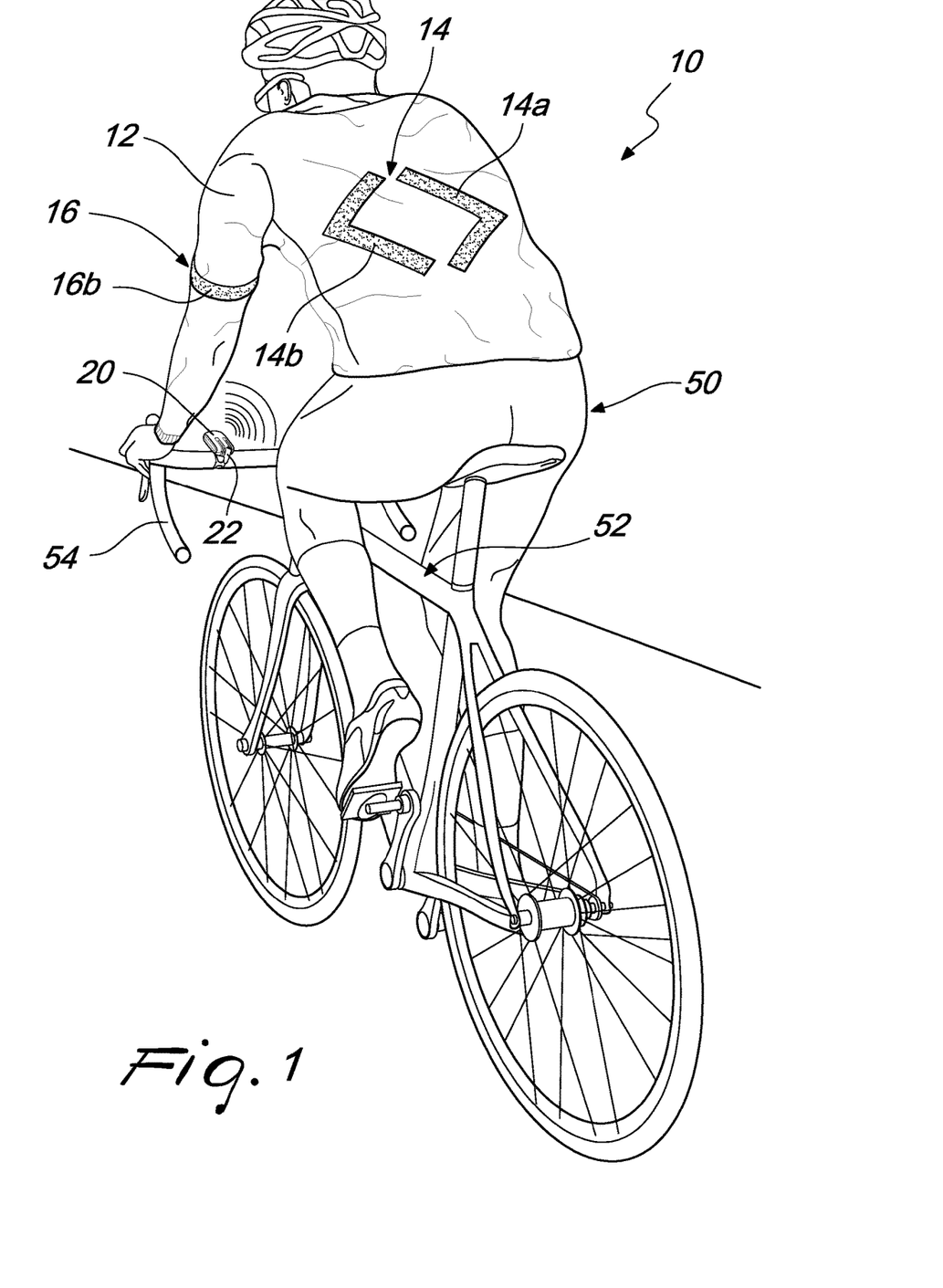
FIG. 1 shows a preferred embodiment of the smart safety garment with signal lights, according to the disclosure.
Figure 2:
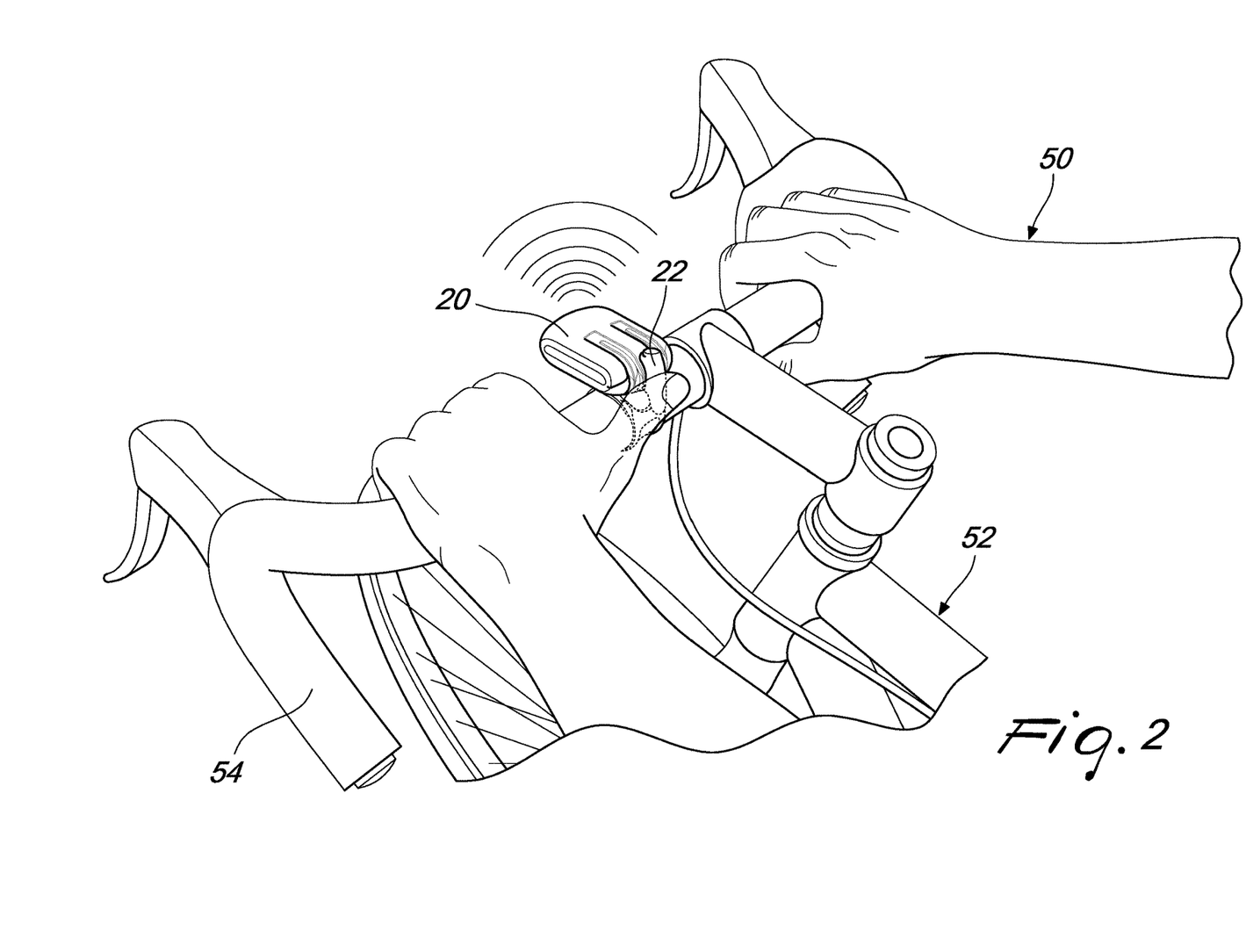
FIG. 2 shows a detail of the preferred embodiment of the smart safety garment with signal lights, according to the disclosure, shown in FIG. 1.
Figure 3:
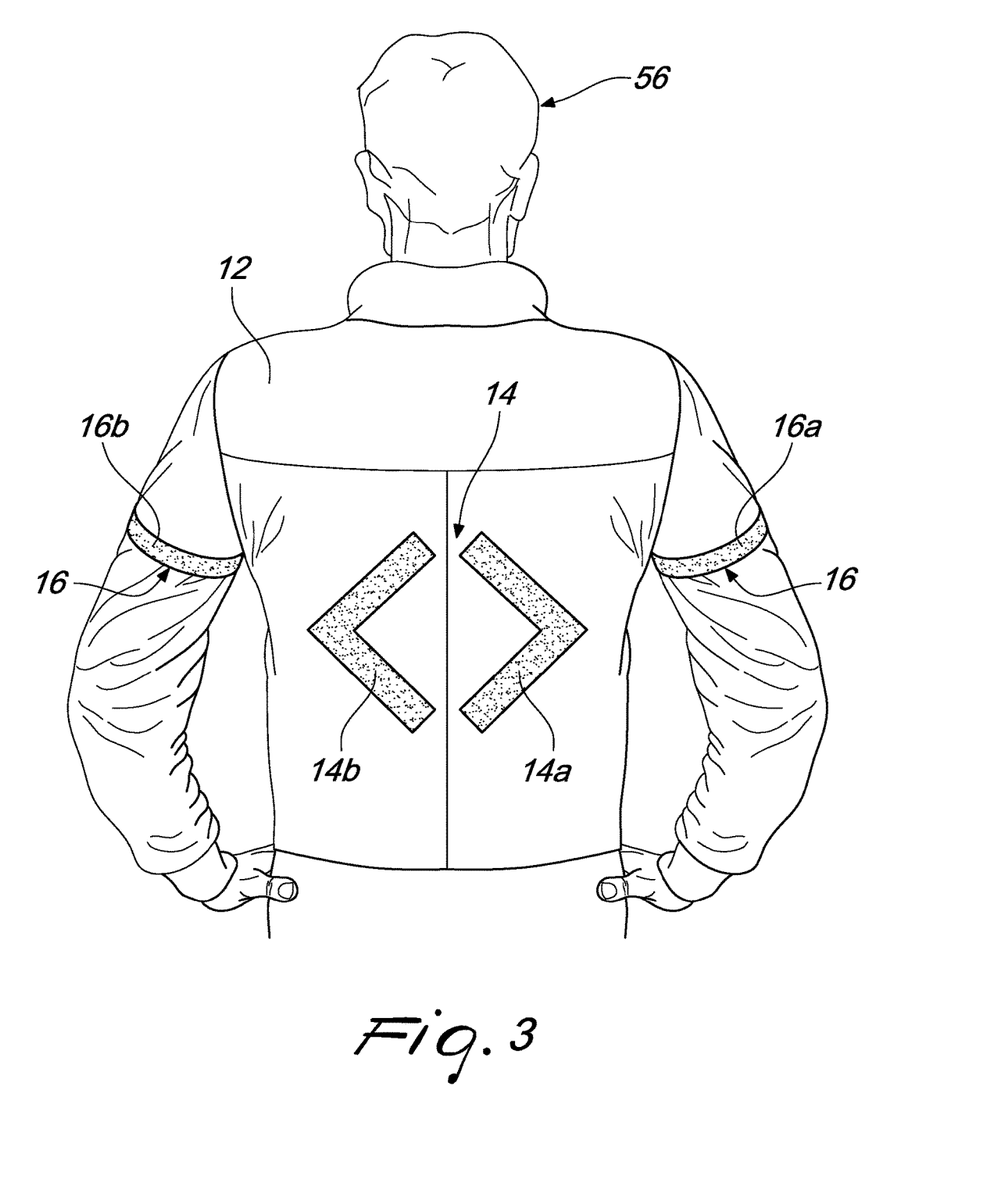
FIG. 3 shows a preferred embodiment of the smart safety garment with signal lights, according to the disclosure.
Figure 4:
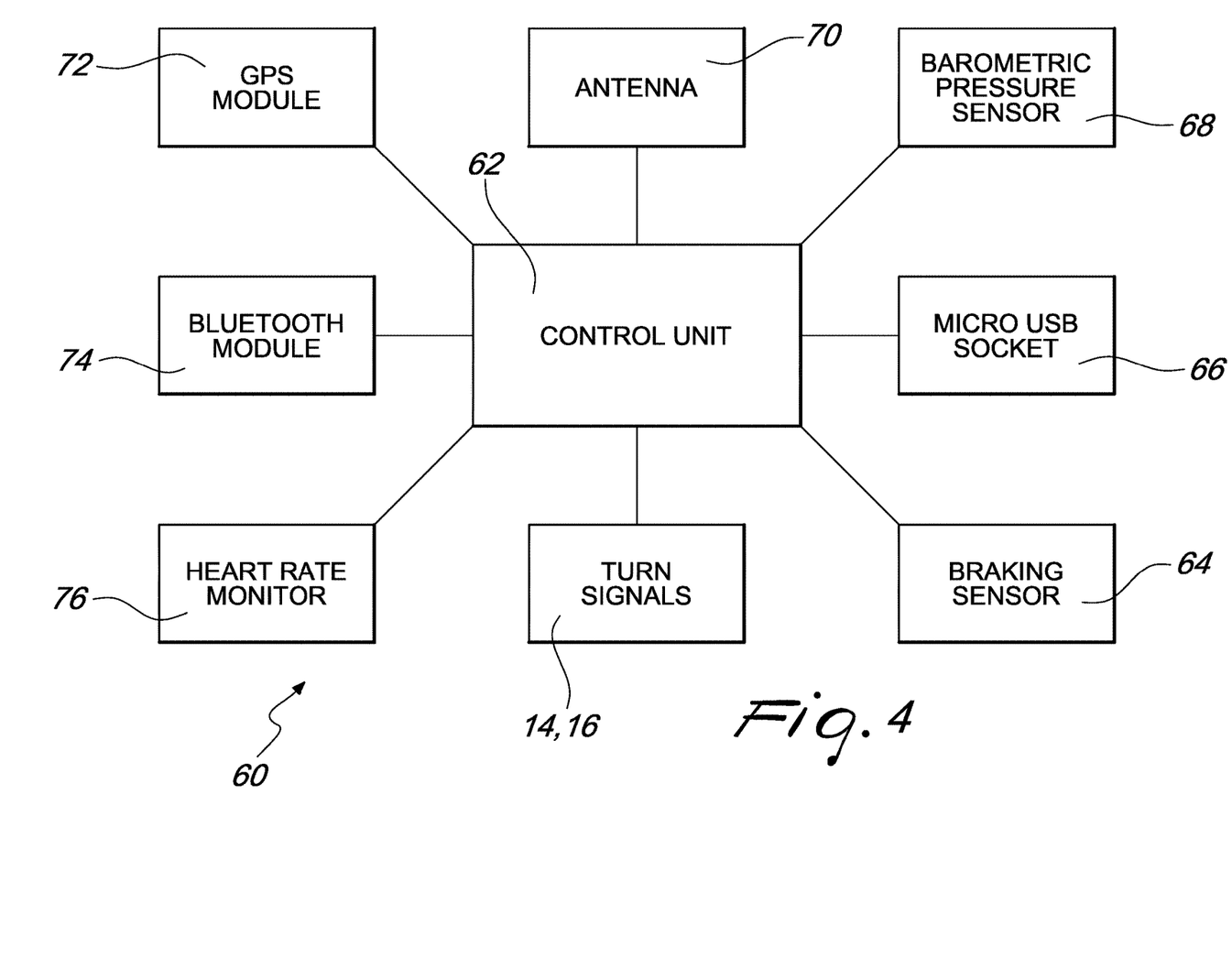
FIG. 4 is a block diagram of a preferred embodiment of the electronic assembly of the smart safety garment with signal lights according to the disclosure.

The electronic assembly 60 of the smart safety garment 10 comprises a control unit 62, which has control functions within the smart safety garment 10, since it powers up the turn signal lights 14 and 16, connected or connectable to it, according to the commands coming from the remote control 20 or to the information coming from a braking sensor 64, as well as it manages the data coming from an optional barometric pressure sensor 68, an optional GPS module 72, and an optional heart rate monitor 76.

The control unit 62 is configured to receive one or more signals representative of one or more conditions, such as the commands coming from the remote control 20, or the deceleration of the bicycle 52 perceived by a braking sensor 64. The control unit 62 is also configured to power up the turn signal lights 14 and 16 connected to it according to the signals previously received by the control unit 62, so that they emit light according to the conditions.

In a preferred embodiment, the control unit 62 is a wireless Microcontroller Unit (MCU), which combines a high performance RF radio and a microcontroller with extremely low power consumption.

Even though any type of microcontroller can be used to manage the smart safety garment 10 according to the disclosure, the microcontroller is preferably selected of a type of microcontrollers characterized by their extremely low power consumption.

The other components of the electronic assembly 60 of the smart safety garment 10 may be connected or connectable to the control unit 62 separately, for example by means of wires, or together, for example through a bus.

The signal representative of the deceleration condition originates from the braking sensor 64, which is able to detect the deceleration and to automatically report this condition to the control unit 62.

The electronic assembly 60 of the smart safety garment 10 comprises a braking sensor 64, connected or connectable to the control unit 62, which is adapted to perceive the deceleration when the cyclist 50 is braking and to generate a corresponding braking signal intended to the control unit 62, in order to power up the turn signal lights 14 and 16 according to this braking signal (brake mode, see below).

In a preferred embodiment, the braking sensor 64 may comprise a built-in three-axis accelerometer, or a more sophisticated Inertial Measurement Unit (IMU), including a combination of accelerometers and gyroscopes.

With the braking sensor 64, the control unit 62 can automatically activate the brake mode of the smart safety garment 10 when the cyclist 50 is braking, preventively warning upcoming car drivers and promptly alerting them to the slowdown of the cyclist 50, so as to enable the drivers to react in time thereby avoiding possible road accidents.

The smart safety garment 10 according to the disclosure is powered by an energy source (not shown in the drawings) included in the electronic assembly 60 and connected or connectable to the control unit 62. In a preferred embodiment, the energy source is embedded in the basic garment 12.

The control unit 62 has control functions within the smart safety garment 10, and it also controls the power supply of the components of the electronic assembly 60.

For example, the energy source may be a tiny, long life, rechargeable battery, so that the user 50, 56 doesn't have to often take care about recharging. In a preferred embodiment, a possible battery may be a lithium-ion polymer (LiPo) battery, or an equivalent battery.

In a preferred embodiment, the electronic assembly 60 of the smart safety garment 10 may further comprise a socket 66, preferably of micro USB type, connected or connectable to the control unit 62, which is adapted to connect the smart safety garment 10 and recharge easily the battery of the smart safety garment 10 by means of a wall socket or a computer, such as a laptop PC or a desktop PC.

The micro USB socket 66 may be also adapted to connect the smart safety garment 10 to a computer in order to allow the user 50, 56 to configure the smart safety garment 10 itself, in particular the control unit 62, and to download all the data gathered during the user' activity.

The socket 66 can be hidden into the shoulder area of the basic garment 12 in the form of a jacket.

In order to perform the wireless reception of the command signals, such as RF signals, that are generated by the remote control 20 operated by the cyclist 50 and that carry the commands for the control of the turn signal lights 14 and 16, the electronic assembly 60 of the smart safety garment 10 comprises an antenna 70, connected or connectable to the control unit 62, for receiving the RF command signals from the remote control 20.

In summary, these commands are sent from the remote control 20 to the electronic assembly 60 of the smart safety garment 10 by means of the respective antennas, for example RF antennas.

The present disclosure is also suitable for those cyclists, but also for those pedestrians, such as runners and joggers, who want to track and then analyse their personal fitness parameters and their performances history, following the growing trend of personal data collection.

The smart safety garment 10 may be equipped with sensors, described in detail below, in order to gather and then analyse various fitness and health parameters of the user 50, 56.

In a preferred embodiment, the electronic assembly 60 of the smart safety garment 10 may further comprise a GPS module 72 and a barometric pressure sensor 68, both connected or connectable to the control unit 62. The combination of the GPS module 72 and the barometric pressure sensor 68 allows to accurately measure, gather and store data concerning the user' activity, such as for example average speed, distance covered, duration, pace, rate of climb and grade, calories burned, and other similar useful tracking data. All these data are stored in a dedicated or shared memory (not shown in the drawings) passing through the control unit 62.

In a different embodiment of the disclosure, the electronic assembly 60 of the smart safety garment 10 may further comprise only the GPS module 72 and not the barometric pressure sensor 68, or it may further comprise only the barometric pressure sensor 68 and not the GPS module 72.

In a preferred embodiment, the electronic assembly 60 of the smart safety garment 10 may further comprise a heart rate monitor 76, connected or connectable to the control unit 62, which is adapted to measure the heartbeat in real time, for example the heartbeat of the cyclist 50 or of the pedestrian 56, and to store it in a dedicated or shared memory, not shown in the drawings, passing through the control unit 62. This heart rate monitor 76 is preferably hidden into the wristband of the basic garment 12 in the form of a jacket.

In a preferred embodiment, the electronic assembly 60 of the smart safety garment 10 may further comprise a Bluetooth module 74, preferably of Bluetooth low energy (BLE) type, connected or connectable to the control unit 62, which is adapted to connect via Bluetooth the smart safety garment 10 to a mobile device, for example a smartphone properly configured by means of a mobile software application.

This communication allows the user 50, 56 to configure the smart safety garment 10, in particular the control unit 62, via smartphone, and to download all the data gathered and stored during the user' activity and visualize them as simple indicators and charts, that the user 50, 56 can monitor daily.

When the smart safety garment 10 communicates with the smartphone's application, via Bluetooth, all the gathered and stored data may be synched and plotted into charts that help the user 50, 56 to monitor his/her performances history, for example to build healthy lifestyle habits and to achieve personal goals.

In a preferred embodiment of the disclosure, the smart safety garment 10 may offer a plurality of operating modes, namely a plurality of activation modes of the turn signal lights 14 and 16. The following items outline some preferred operating modes offered by the smart safety garment 10 according to the disclosure:

Turn signals mode (right or left): moving to the desired direction the lever 22 of the remote control 20 positioned on the handlebars 54 of the bicycle 52, an orange light is emitted by the turn signal lights 14 and 16 corresponding to the desired direction (right: 14a and 16a; left: 14b and 16b);

Brake mode: automatically activated when the braking sensor 64 perceive the deceleration when the cyclist 50 is braking, a red light is emitted by all the turn signals 14 and 16;

Turn signals and brake mode: automatically activated when the cyclist 50 is moving to the desired direction the lever 22 of the remote control 20 and the braking sensor 64 perceive the deceleration when the cyclist 50 is braking, alternate orange and red lights are emitted by all the turn signals 14 and 16;

Solid mode: operating the switch or button placed directly on the basic garment 12, a white light is emitted by all the turn signals 14 and 16;

Strobe mode: operating the switch or button placed directly on the basic garment 12, an alternate white light is emitted by all the turn signals 14 and 16.

In the light of the above, it has been ascertained that the smart safety garment with signal lights according to the present disclosure achieves the intended aim in an effective manner, since it allows to improve the safety of urban cyclists and pedestrians, such as runners and joggers, avoiding possible road accidents, enhancing their visibility along streets with poor light conditions, also from long distances.

A further advantage of the disclosure is that it permits a cyclist or a pedestrian to not worry about the control of the signal lights, automating and simplifying as much as possible their operation. Moreover, it allows a cyclist to not move his/her hands from the handlebars of the bicycle, if he/she needs to directly control the signal lights.

Although the smart safety garment with signal lights according to the disclosure have been conceived in particular to improve the safety of urban cyclists, enhancing their visibility along streets with poor light conditions, it can be used in any case more generally to improve the safety of any person who moves on the streets, for example also urban pedestrians, such as runners and joggers, enhancing their visibility along streets with poor light conditions.

The disclosure thus devised is susceptible of numerous modifications and variations, all of which are within the scope of the inventive concept; all the details may furthermore be replaced with other technically equivalent elements.

In practice, the materials used, as well as the dimensions, may be any according to the requirements and the state of the art.

One skilled in the art will realize the disclosure may be embodied in other specific forms without departing from the disclosure or essential characteristics thereof. The foregoing embodiments are therefore to be considered in all respects illustrative rather than limiting of the disclosure described herein.

The invention claimed is:

1. A smart safety garment with signal lights comprises a garment, at least a pair of turn signal lights embedded on the external surface of said garment, and an electronic assembly for the control, management and monitoring of said smart safety garment comprising a control unit, said at least a pair of turn signal lights being connected or connectable to said control unit, wherein said electronic assembly further comprises a braking sensor, connected or connectable to said control unit, adapted to perceive a deceleration and to generate a corresponding braking signal to said control unit and a barometric pressure sensor, connected or connectable to said control unit, said control unit being configured to power up said at least a pair of turn signal lights according to said braking signal.

2. The smart safety garment with signal lights according to claim 1, wherein said at least a pair of turn signal lights comprises multi-color (RGB) light emitting diodes (LEDs).

3. The smart safety garment with signal lights according to claim 2, wherein the light emitted by said RGB LEDs is diffused into an optical flat light guide.

4. The smart safety garment with signal lights according to claim 1, wherein said braking sensor comprise a built-in three-axis accelerometer or an Inertial Measurement Unit (IMU).

5. The smart safety garment with signal lights according to claim 1, wherein said control unit is a wireless Microcontroller Unit (MCU).

6. The smart safety garment with signal lights according to claim 1, wherein said smart safety garment further comprises control means, operable by a user for the control of said at least a pair of turn signal lights, adapted to generate a command signal to said control unit, said control unit being configured to power up said at least a pair of turn signal lights according to said command signal.

7. The smart safety garment with signal lights according to claim 6, wherein said control means comprises a remote control placed or placeable on the handlebars of a bicycle.

8. The smart safety garment with signal lights according to claim 6, wherein said control means comprises a switch, connected or connectable to said control unit, placed directly on said garment.

9. The smart safety garment with signal lights according to claim 1, wherein said electronic assembly further comprises a GPS module, connected or connectable to said control unit.

10. The smart safety garment with signal lights according to claim 1, wherein said electronic assembly further comprises a heart rate monitor, connected or connectable to said control unit.

11. The smart safety garment with signal lights according to claim 1, wherein said electronic assembly further comprises a Bluetooth module, connected or connectable to said control unit, for the communication of said smart safety garment with a mobile device.

12. The smart safety garment with signal lights according to claim 1, wherein said electronic assembly further comprises an energy source, connected or connectable to the control unit.

13. The smart safety garment with signal lights according to claim 12, wherein said energy source is a lithium-ion polymer (LiPo) battery.

14. The smart safety garment with signal lights according to claim 1, wherein said electronic assembly further comprises a socket, connected or connectable to said control unit.

15. The smart safety garment with signal lights according to claim 14, wherein said socket is of micro USB type.

\* \* \* \* \*